(12) United States Patent
DeCenso et al.

(10) Patent No.: US 7,516,851 B2
(45) Date of Patent: Apr. 14, 2009

(54) RETAINER FOR AN ELECTRONIC COMMUNICATION DEVICE TO DETECT BREAKS IN POROUS ELEMENT SEPARATOR

(75) Inventors: Anthony J. DeCenso, Cincinnati, OH (US); Michael Timmerman, Cincinnati, OH (US)

(73) Assignee: M-I L.L.C., Houston, TX (US)

( * ) Notice: Subject to any disclaimer, the term of this patent is extended or adjusted under 35 U.S.C. 154(b) by 519 days.

(21) Appl. No.: 11/120,702

(22) Filed: May 3, 2005

(65) Prior Publication Data

US 2005/0247603 A1 Nov. 10, 2005

Related U.S. Application Data

(63) Continuation-in-part of application No. 10/668,114, filed on Sep. 22, 2003, now Pat. No. 6,997,325.

(51) Int. Cl.
*B07B 1/49* (2006.01)
(52) U.S. Cl. ........................ 209/420; 209/421; 455/66.1
(58) Field of Classification Search ................ 209/420, 209/421; 455/66.1, 556.1
See application file for complete search history.

(56) References Cited

U.S. PATENT DOCUMENTS

| | | |
|---|---|---|
| 3,725,666 A | 4/1973 | Berthold |
| 3,960,001 A | 6/1976 | Hayes |
| 4,022,693 A | 5/1977 | Morgan, Jr. |
| 4,251,354 A | 2/1981 | Lower |
| 4,582,597 A | 4/1986 | Huber |
| 4,613,432 A | 9/1986 | Racine et al. |
| 4,655,911 A | 4/1987 | Tabor |
| 4,968,366 A | 11/1990 | Hukki et al. |
| 5,032,210 A | 7/1991 | Hukki et al. |
| 5,051,171 A | 9/1991 | Hukki |
| 5,134,893 A | 8/1992 | Hukki et al. |
| 5,221,008 A | 6/1993 | Derrick, Jr. et al. |
| 5,226,546 A | 7/1993 | Janssens et al. |
| 5,242,058 A | 9/1993 | Jones |

(Continued)

FOREIGN PATENT DOCUMENTS

JP 2004-205298 7/2004

OTHER PUBLICATIONS

International Search Report and Written Opinion issued Sep. 29, 2006 for International Application PCT/US2006/016662, filed May 2, 2006.

*Primary Examiner*—Patrick H Mackey
*Assistant Examiner*—Terrell H Matthews

(57) ABSTRACT

A retainer holds an electronic communication device used to detect breaks in porous elements of material separators to the frame of the separator. The retainer includes a ferrule affixed around a hole through the frame of the separator, a housing made from an RF transmissible material sealingly held within the ferrule, and a cap sealingly held against the ferrule. The electronic component is held by the cap such that it is situated within the housing. Such a retainer is affixed to frames of the separator on opposing sides of a porous element so that a transmitter may be retained in a first retainer and a receiver retained in a second retainer. The transmission of a signal from the transmitter that is received by the receiver indicates a break in the porous element between the components.

5 Claims, 10 Drawing Sheets

U.S. PATENT DOCUMENTS

| | | |
|---|---|---|
| 5,255,789 A | 10/1993 | Janssens et al. |
| 5,265,730 A | 11/1993 | Norris et al. |
| 5,271,504 A | 12/1993 | Bowen et al. |
| 5,456,365 A | 10/1995 | Janssens et al. |
| 5,950,841 A | 9/1999 | Knox et al. |
| 5,996,807 A * | 12/1999 | Rumpf et al. ............... 209/401 |
| 6,089,380 A * | 7/2000 | Hazrati et al. ............... 210/411 |
| 6,202,856 B1 | 3/2001 | Carr |
| 6,349,834 B1 | 2/2002 | Carr et al. |
| 6,431,368 B1 | 8/2002 | Carr |
| 6,443,010 B1 | 9/2002 | Scofield |
| 6,513,665 B1 | 2/2003 | Hukki et al. |
| 6,585,116 B1 * | 7/2003 | Doelle et al. ................ 209/305 |
| 6,964,694 B2 | 11/2005 | Rauchfuss et al. |
| 6,997,325 B2 | 2/2006 | DeCenso |
| 7,343,136 B2 * | 3/2008 | Liu et al. .................... 455/66.1 |

* cited by examiner

RETAINER FOR AN ELECTRONIC COMMUNICATION DEVICE TO DETECT BREAKS IN POROUS ELEMENT SEPARATOR

This application is a continuation-in-part of U.S. application Ser. No. 10/668,114, filed Sep. 22, 2003 now U.S. Pat. No. 6,997,325 the contents of which are incorporated herein by reference.

BACKGROUND OF THE INVENTION

Separator systems are used in industry for a variety of undertakings. They are used to process dry materials and liquid/solid slurries. Each one typically functions by first introducing a flow of material to a porous element such as a screen or filter, usually of woven wire mesh or a porous membrane. The flow of material is separated into two streams, one containing material that passes through the porous element, the other containing material that is rejected by the porous element. A drive mechanism may be operatively coupled with a housing to produce a vibrating motion that serves to put the material on the porous element in motion until it either passes through or is pushed off the element at the periphery thereof. Other devices use pressure to increase flow through a membrane with cycled application including reverse flow to clear the rejected material.

Such separator systems employ screens in rectangular and circular forms with screen elements tensioned on frames or with hooks tensioned on the separator itself. The screen elements range greatly in porosity and can be of a single element or of laminated elements. The separator frames can be vibratory or fixed and, when vibratory, supported by a variety of means such as springs, bushings or links. Such systems alternatively employ filters, tensioned or untensioned, supported or unsupported and of widely varying porosities and shapes including rectangular, circular, cylindrical and bag shaped. Many additional features are, of course, available such as housing covers, elaborate manifolds and various and changeable motions, rates and cycles. Patents disclosing a small sampling of such systems and components include U.S. Pat. Nos. 4,022,693; 4,251,354; 4,582,597; 4,613,432; 4,655,911; 4,968,366; 5,032,210; 5,051,171; 5,134,893; 5,221,008; 5,226,546; 5,242,058; 5,255,789; 5,265,730; 5,271,504; 5,456,365; 5,950,841; 6,089,380; 6,202,856; 6,349,834; 6,431,368; and 6,513,665, the disclosures of which are incorporated herein by reference.

Materials typically screened vary considerably in their particle size, bulk density, chemical composition, temperature, moisture content and other physical and chemical characteristics. Any particular separator system in a given processing plant is likely dedicated to handling a single material with consistent properties. Examples of such materials, to show the diversity but not to provide a comprehensive list, include: abrasives, activated carbon, calcium carbonates, ceramic slurries, chlorine compounds, citric acid, fertilizers, flours, food products, gunpowder, minerals, paper coating slurries, pharmaceuticals, pigments, polystyrene beads, powdered metals, powdered paints, printing inks, PVC powder, refractories, rocket propellants, and starches.

As a result, various screen configurations, vibration profiles and environments are employed to maximize efficiency and the quality of the resulting processed materials.

By far the most common failure mode for separator systems is the failure of the porous element. Screens, for example, are typically made of finely woven wire cloth drawn taut by a screen frame or tensioning apparatus on the separator. Failure is caused by numerous factors such as wear and fatigue failure. Such failures typically occur as breaks in the screening media itself resulting in a damaged screen. Such breaks may manifest themselves as tears (a series of mutually adjacent broken wires), punctures (tears in two directions) or holes (missing portions of the screening material). Once the screen has failed, the function of a separating system is compromised. At a minimum, it can no longer be relied upon to reject all oversized material because such material can now pass through the break in the screen. Worse, it can result in fragments of the failed screen contaminating the material being screened, presenting a serious hazard in food or pharmaceutical screening operations. Similar failure occur in filter elements.

As the porous elements are typically located within closed housings or under material being processed, it is difficult to visually detect such failures. Thus, where critical separation is demanded, frequent inspection is advisable. As such efforts to insure quality separation result in downtime and labor and still result in compromised processed material, methods for detecting breaks have been long sought. Systems have been devised that attempt to detect screen failure by measuring the electrical or optical paths through the mesh screen itself. See U.S. Pat. No. 5,996,807, the disclosure of which is incorporated herein by reference. These are believed to have been proven impractical and have not met with general market acceptance.

A detection system is most beneficial when it can be retained in a location relative to the porous element(s) under surveillance or being audited. The retaining system must be transparent to the detection system while keeping it in a fixed location during operation of the material separator. Thus, a retaining system must firmly affix the detection system to the material separator in a desired location. Further, a retaining system must not interfere with the operation of the detection system or the material separator while protecting the detection system from being infiltrated with material from the separator. In addition, the retaining system should allow access to the detection system for maintenance or use of the detection system on another material separator.

SUMMARY

In one aspect, the claimed subject matter is generally directed to a retainer for a component of an electronic communication device used to detect a break in a porous element in a material separator. The material separator includes a first frame and a second frame. The first frame has a first frame wall and the second frame has a second frame wall. The porous element is retained between the first frame wall and the second frame wall. A first chamber is defined by the first frame wall and the porous element and a second chamber is defined by the second frame wall and the porous element. The first frame wall has an RF path through it. The retainer includes a ferrule having a first end affixed to the outer surface of the first frame wall around the RF path. The second end of the ferrule extends outward from the first frame wall. A housing is sealingly retained within the ferrule. The housing physically separates the component of the electronic communication device from the first chamber to protect the communication device from the coming into contact with product in the first chamber. The electronic communication device component is retained by the cap, which holds the component within the housing. The cap and the ferrule second end are sealingly retained together.

The RF path through the first frame wall must remain the exclusive path of RF signals to or from the electronic communication device component. The ferrule and cap may be made from a material preventing the transmission of RF signals through them. The housing may be made from a material through which RF signals are transmissible, thereby providing RF communication between the electronic communication device component and the first chamber. A shield may be included to shield a receiver antenna from noise due to other electronic components in the detection system.

The ferrule may include a flange against which the cap is sealing retained. A clamp band may be used to retain the ferrule flange to the cap. The housing may also include a flange, retained between the ferrule flange and the cap. Alternatively, the cap may be screwed onto the ferrule with a sealing material placed between them. In another alternative, the cap may be sealingly retained within the housing by an o-ring or other type of compression fit device.

In a separate aspect of the present invention, a retaining system for a transmitter and a receiver is claimed. A first retainer houses the transmitter so that RF signals are transmitted to the first chamber through the RF path in the first frame wall. The second frame wall has an RF path through it to the second chamber and a second retainer houses the receiver so that RF signals may be transmitted from the second chamber to the receiver through the RF signal in the second frame wall. Each retainer may have the embodiments previously described.

Other aspects and advantages of the claimed subject matter will be apparent from the following description and the appended claims.

DETAILED DESCRIPTION

Figure 12:
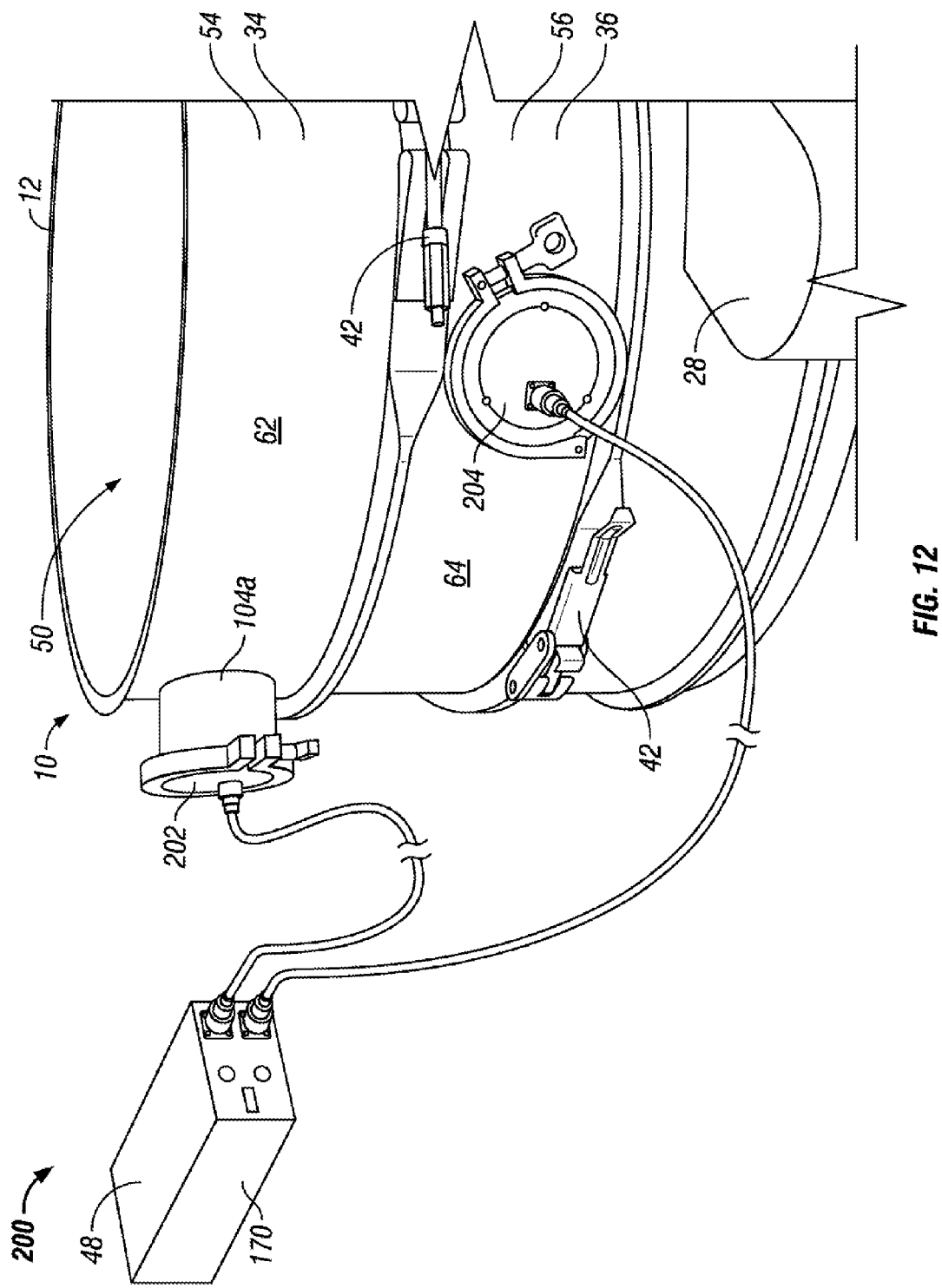
FIG. 12 is a perspective view of an embodiment of a retainer system.
Figure 13:
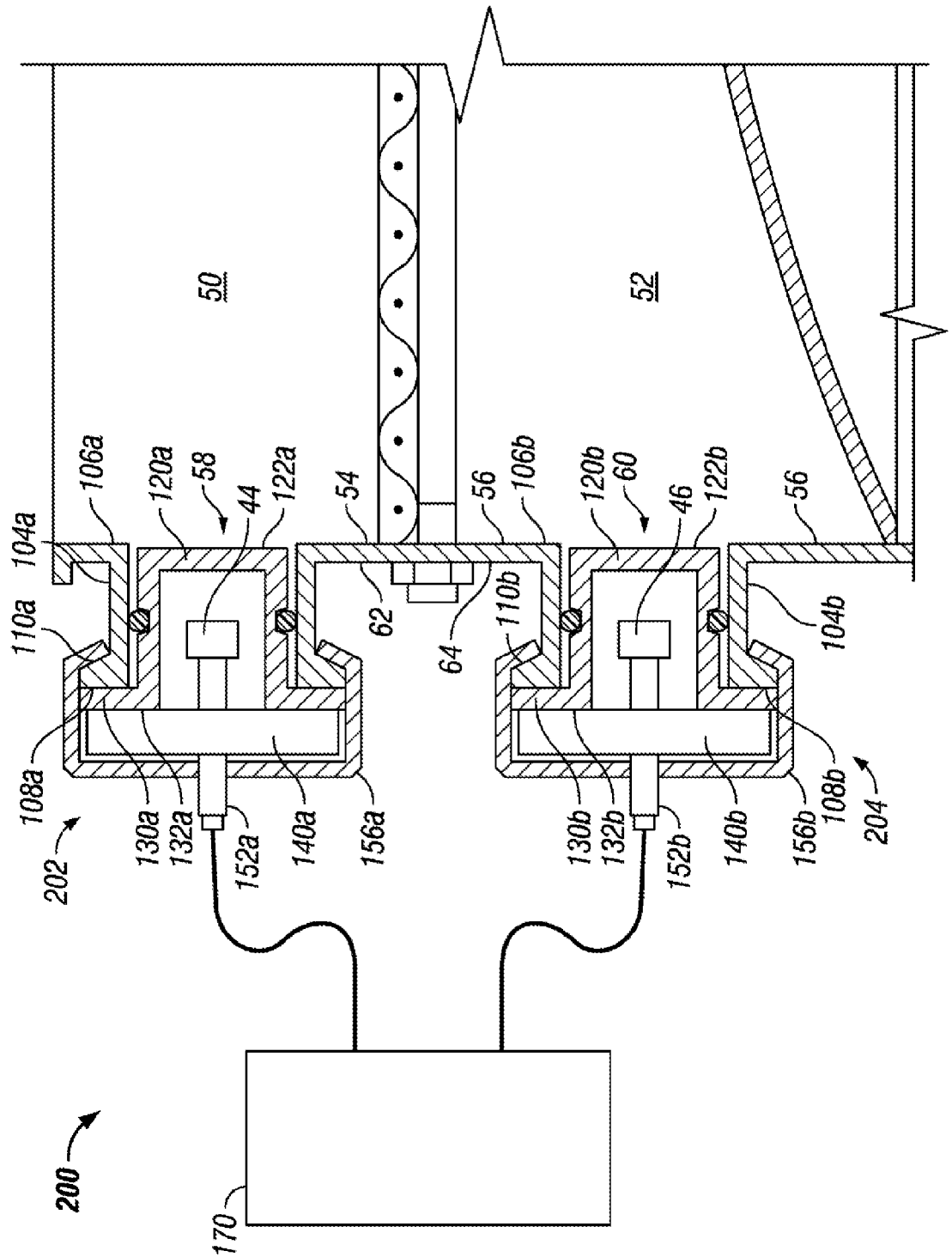
FIG. 13 is a cross sectional side view of an embodiment of a retainer system.

The claimed subject matter relates to a retainer 100 for a component of an electronic communication device, depicted in FIGS. 3-7 and a retainer system 200 for an RF transmitter 44 and a receiver 46, shown in FIGS. 12 and 13. The retainer 100 and the retainer system 200 are used to detect breaks in a porous element in a material separator 10.

Figure 1:
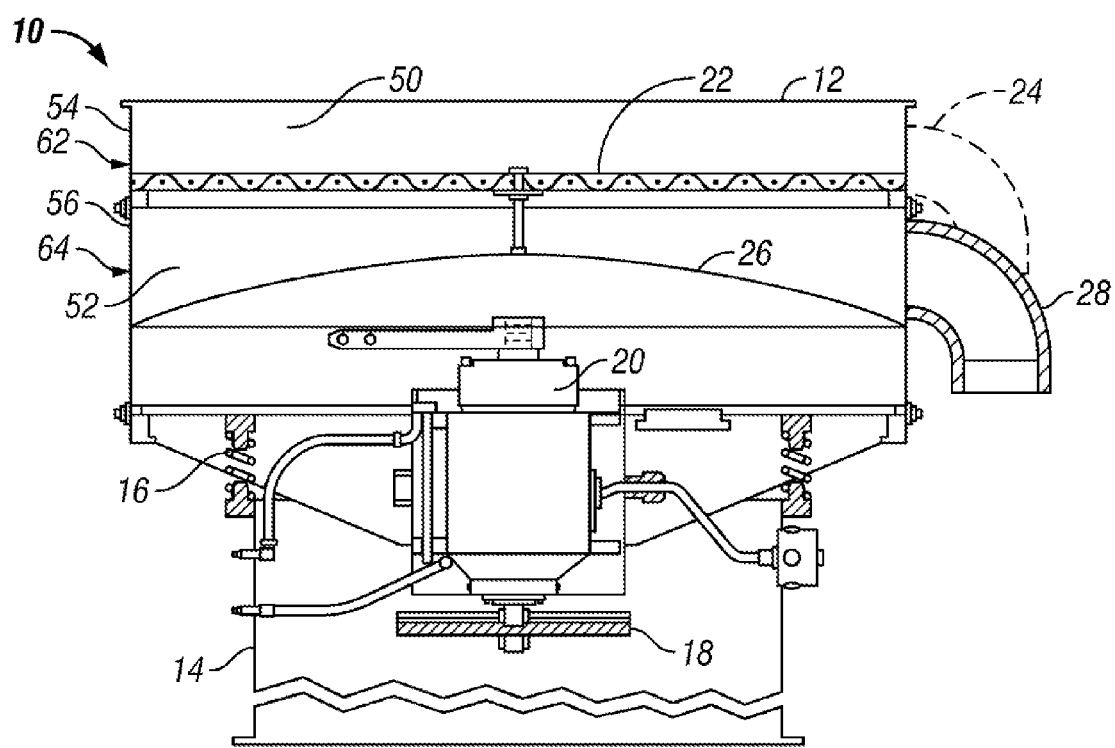
FIG. 1 is a side view of a material separator.

Turning in detail to the drawings, FIG. 1 illustrates a conventional vibratory screen material separator, generally designated 10, to provide context for one material separation system for detecting breaks in a porous element. Nonvibratory screening systems and filtration systems in a range of such systems described above in the Background of the Invention can also find increased utility with a system for detecting breaks in the porous element employed for material separation.

The separator 10 includes a separator housing 12 which is elastically mounted to a base 14 on springs 16. A vibration generator 18 driven by a motor 20 causes the elastically mounted separator housing 12 to vibrate at an advantageous frequency and amplitude for material screening or filtering. A porous element, which is a screen 22 in this embodiment, extends across the separator housing 12 to separate material deposited thereon by selected characteristics. An overs outlet 24 may be present above the screen 22 while below the screen 22 may be a domed manifold 26 which feeds a throughs outlet 28.

Figure 2:
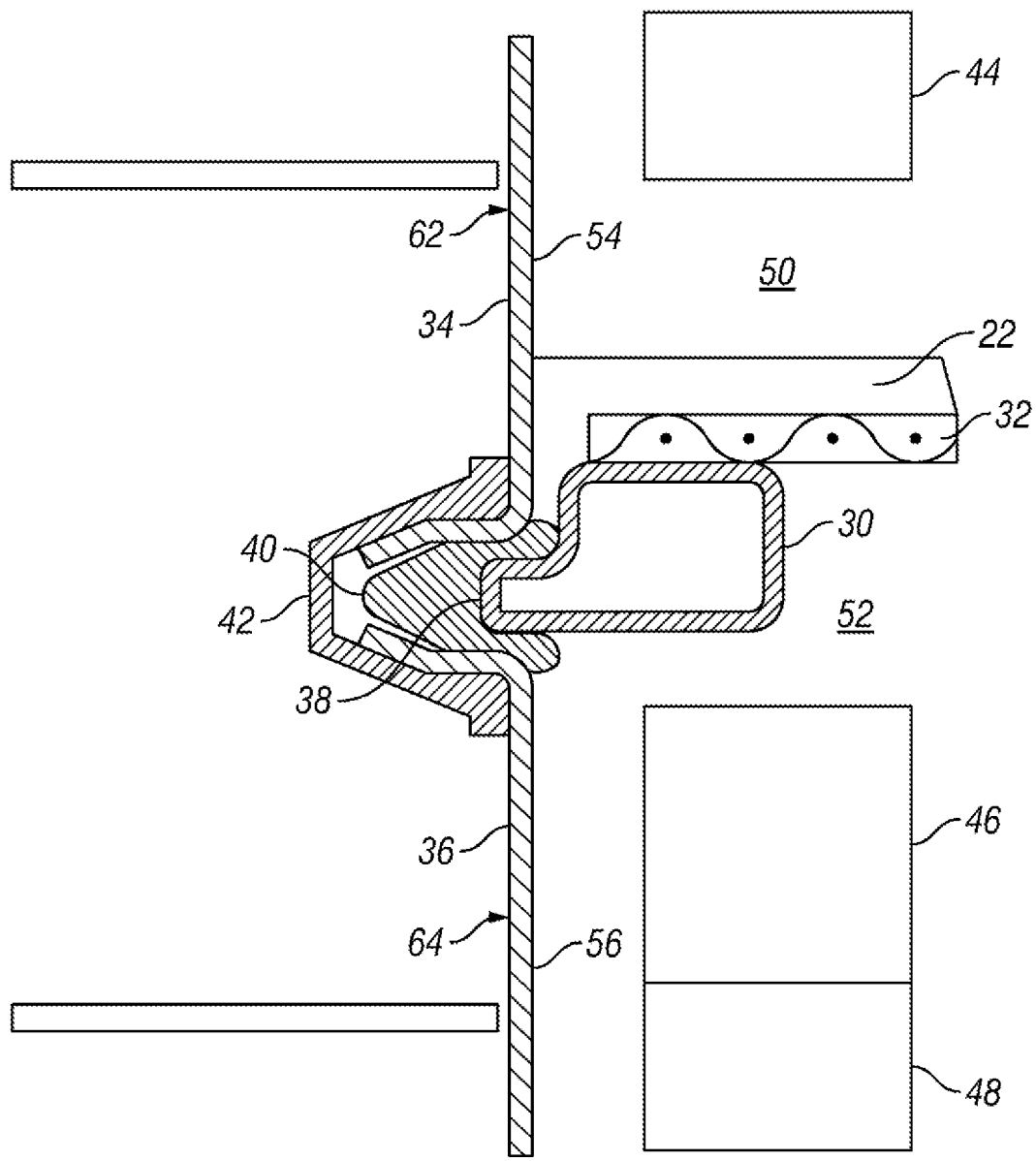
FIG. 2 is a housing seal arrangement associated with a material separator and an electronic communication device as associated therewith.

Referring to FIG. 2, the seal arrangement and construction of the separator housing 12 about the screen 22 is illustrated. Also illustrated are details of the porous element, defined in this embodiment as a screen 22. The screen 22 includes a screen frame 30 which may be a formed metal ring. Screen cloth 32 is bonded to the screen frame 30 in a taut state. The screen cloth 32 is typically wire mesh of electrically conductive stainless steel. Preconfigured interstices are defined by the weave, the wire diameter and the wires per unit measure.

The separator housing 12 is shown to be of at least two cylindrical frames 34 and 36. These frames 34 and 36 come together about a flange 38 on the screen frame 30. As such, a screen mount is defined therebetween fully about the interior of the separator housing 12. A gasket 40 is positioned about the flange 38 and a clamp band 42 draws the entire assembly together. The entire separator 10 also is contemplated to include a cover with an inlet therein through which material is delivered to the screen 22.

In creating a first chamber 50 and a second chamber 52 within the separator housing 12 which includes a barrier to an RF signal, the frames 34 and 36 are electrically conductive. The cover (not shown) might also be electrically conductive as well as the domed manifold 26 beneath the screen 22. The overs outlet 24 and the throughs outlet 28 can also be electrically conductive and further electrically conductive shielding as may be needed is contemplated to prevent transmission of the RF signals therethrough. Further, the gasket 40 is anticipated to be electrically conductive or to require an electrically conductive barrier to prevent the RF signals from flowing around the screen frame 30 within the screen mount. The conductivity is provided through the employment of sheet metal components acting to create a barrier to the RF signals.

With the aforementioned components, the separator housing 12 may define a chamber having a barrier to the RF signals either above or below the screen 22. Above the screen 22, the first frame 34, the overs outlet 24, the gasket 40, and a cover (not shown), along with other shielding as may be required, define a first chamber 50. Below the screen 22, the second frame 36, the domed manifold 26, the throughs outlet 28 and the gasket 40, again with additional shielding as may be needed, may define a second chamber 52 with a barrier to the RF signals.

Between these two defined spaces, whether both form a chamber or only one forms a chamber with an RF barrier, a path exists through the screen mount. Without the screen 22, material to be processed has a clear path, as do the RF signals. The screen 22, positioned across this path in the screen mount defined by the separator housing 12 creates a selective path for material being processed according to selected characteristics. By selecting the appropriate RF signal, the screen 22 of conductive metal wire can act as a barrier to substantially attenuate, including to the point of virtual elimination, the RF signal passage along the path across the screen 22 so long as the preconfigured interstices of the unbroken screen remain intact. The screen 22 having interstices in the range of commercial screening systems is a barrier to RF signals in the microwave range. Other porous elements including screens and membranes which block microwaves in addition to woven wire screen cloth can be employed. As one example, electrically conductive coating on nonconductive substrates may adequately block RF signals in the appropriate range.

In the preferred embodiment, the porous element defined by the screen 22, which embodies a barrier across the path between the first and second chambers 50 and 52, is shown to extend in a plane. Instead, the porous element may extend into or out from the main volume of either the first or second chamber 50 or 52 as a filter bag or a cylinder, for example, and the path may, therefore, not necessarily be linear but pass through a porous element mount with the porous element extending fully across the path. The frame retaining the edges of the porous element may be fixed to the porous element as with the screen 22 or may be a mechanism with the separator housing 12, thus becoming part of the porous element mount.

A signal system, illustrated in FIG. 2 schematically, is employed with the vibratory material separator 10 to define a separator system. The signal system includes a signal transmitter 44 and a signal receiver 46 located to either side of the screen 22. The transmitter 44 and the receiver 46 may be mounted to or relative to the first and second frame 34 and 36, respectively. The signal system and the components thereof operate in the RF (radio frequency) range and, more practically given the size of the preconfigured interstices of commercial screens 22, operate in the higher end of the RF range in the microwave range, with the signal system, the transmitter 44 and the receiver 46 being microwave elements. The signals are understood to fall in the range of 700 megaHz to 50 gigaHz with specific empirical tuning to match the characteristics of the screen 22 employed.

Also associated with the microwave signal receiver 46 is a signaling source 48. The signaling source 48 receives input from the receiver 46 and is actuated by the receiver 46 when the receiver 46 receives the microwave signal above a threshold. The threshold is established such that the signaling source 48 does not respond to any substantially attenuated signal passing through a screen 22 without breaks. At the same time, the threshold must also be such that the signaling source 48 is activated when a significant break occurs in the screen 22. Leakage of the RF signal around the screen 22 is to be reduced such that a threshold can be meaningfully set to be activated by a significant break. A significant break in the screen 22 is one that degrades the quality of the throughs resulting from the screening process and is more or less critically significant depending on the material processed. In the case of pharmaceuticals, the quality requirements are far stricter for the end product than in food processing, for example, and degradation in quality is measured by a more critical standard.

When the integrity of the barrier defined by the porous element, in this case the screen 22, fails in any manner which increases an opening size, the length of the resulting opening approaches the wave length of a microwave signal to the point where transmission through that opening can occur. Experiments have shown that detection is likely with the opening achieving one-quarter the wavelength. Screen failures are detected by exploiting this relationship between microwave transmission and electrically conductive barriers.

The signal source 48 recognizes the change in a physical state of the screen 22 when a break occurs through the received RF signal to the receiver 46 and generates a signal as may be desired by the operator, to sound an alarm, to open the power switch to the separator, etc.

In operation the process for detecting breaks during processing of material through the material separator 10 includes the transmission of an RF signal most appropriately in the microwave range and tuned to the RF barrier characteristics of the porous element, the screen 22 in this embodiment, on the first side thereof. The transmitter 44 operates at a frequency with a wave length that is longer than the preconfigured interstices in the screen 22 such that an intact screen will significantly attenuate the signal. Such a differential may be an order of magnitude. With the screen 22 intact, the receiver 46 can be used to define the base line signal transmission characteristics to establish an appropriate threshold. Once a failure has occurred in the screen 22, the resulting enlarged opening will reduce the screen's attenuation of the microwave signal. This allows a stronger signal to reach the receiver 46. Through the use of either analog or digital signal processing techniques, this difference in signal strength is detected and appropriate alarms activated so that the screening process operator can take corrective action Preferably, the microwave system operates continuously and is able to announce a fault as soon as it occurs. While this is preferred, it is not always necessary given that in most processing operations immediate corrective action (such as stopping the line) is not possible. The system can be put to effective use in an intermittent monitoring mode such that it identifies the occurrence of a screen failure within a relative short period of time after its actual occurrence. This time value will vary by industry, but a matter of minutes is sufficient for practically all applications.

Preferably, measurements are made while the separator 10 is operating. In doing so, the microwave system and the screen 22 that is being monitored will be subjected, in conventional equipment, to a magnitude of approximately 2 to 4 G's at a frequency of 4 to 30 Hz depending on the separator used. Alternatively, the separator 10 could be stopped briefly while a measurement is taken.

It is also preferred that measurements be made while the separator 10 is processing material. While doing so, the screen 22 may be covered with material to various depths. With most materials, the RF signal will be able to pass through these depths and not be affected to the point that the signal will not be effective. With problematic materials, inflow to the separator 10 may be turned off while the separator 10 continues to operate. In this way, the processed material is flushed out before a measurement is taken.

In setting up the system, shielding is undertaken. Inherently, separators 10 provide a substantial amount of shielding as they are constructed almost entirely of electrically conductive material such as stainless steel alloys. Sealing about the screen 22 is conventional. However, the seals 40 are typically elastomeric. Further, the ports associated with the overs outlet 24 and throughs outlet 28 provide electrically conductive paths, along with the elastomeric seals 40, for circumventing the path through the screen 22. Electrically conductive material molded into gasket and discharge components, replacement of such components by electrically conductive devices or shielding around these devices themselves can provide adequate signal attenuation such that the receiver 46 can distinguish between screens 22 which are intact and those which have experienced a significant break. Depending on the materials processed, additional events may be sensed such as screen blinding.

Preferably, the transmitter 44 and receiver 46 are retained just outside of the first and second chambers 50 and 52. As the first and second frames 34 and 36 are made from RF shielding material, an RF path 58 through the first frame wall 54 and an RF path 60 through the second frame wall 56 are required as depicted in FIG. 13.

The initial portion of the following discussion will focus on the retainer 100 as a structure and then turn to the retainer 100 as a component of the retainer system 200. Further, the description of the retainer 100 will refer to the first chamber 50, the first frame 34, the first frame wall 54, and the RF path 58 therethrough. One of skill in the art will note that the retainer components described may also apply to the second chamber 52, a second frame, a second wall, etc. The electronic component being retained will generally be referred to as 102, and one of skill in the art will understand that the component 102 may be a transmitter 44 or a receiver 46.

Figure 3:
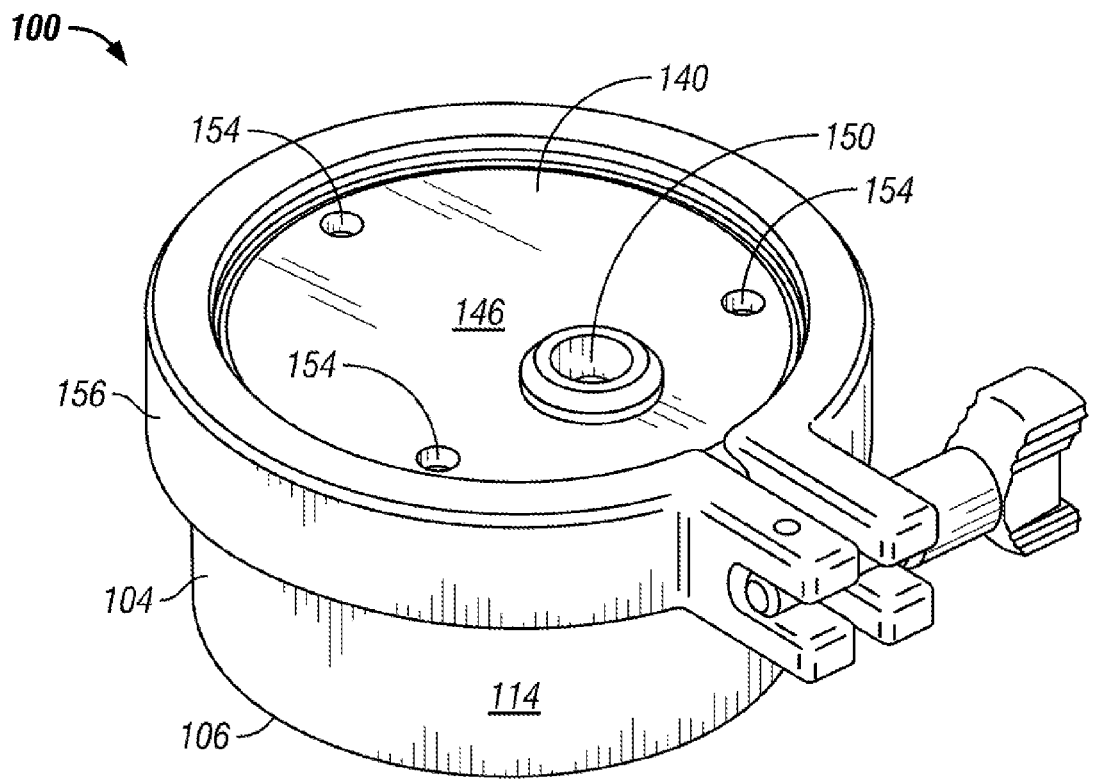
FIG. 3 is a perspective view of an embodiment of a retainer.
Figure 4:
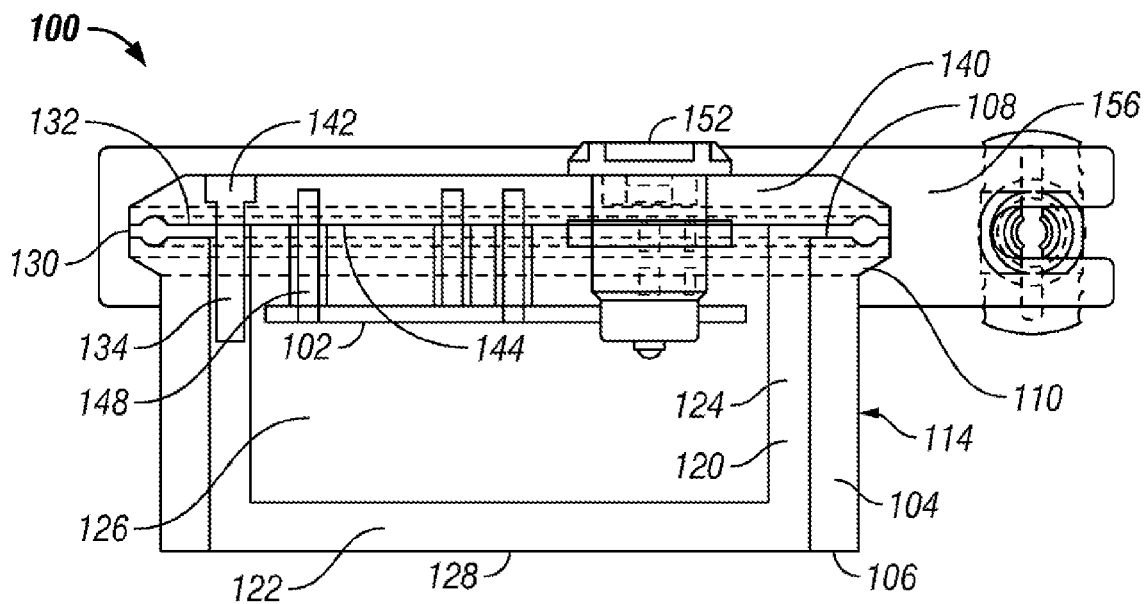
FIG. 4 is a cross sectional side view of an embodiment of a retainer.

Referring to FIGS. 3 and 4, the retainer 100 includes a housing 120 and a cap 140 removably attached to the frame wall 54 at the RF path 58. The retainer 100 and the RF path 58 are sealed in such a manner that RF signals from the retained component 102 are directed only to the first chamber 50 through the RF path 58 as well as preventing product from the first chamber 50 from leaking out through the RF path 58. The cap 140 encloses the component 102 such that RF signals are not emitted away from and outside of the first chamber 50. The cap 140 further provides selective access to the component 102. The component 102 is thus held within a space created within the housing 120 and bounded by the cap 140.

Figure 6:
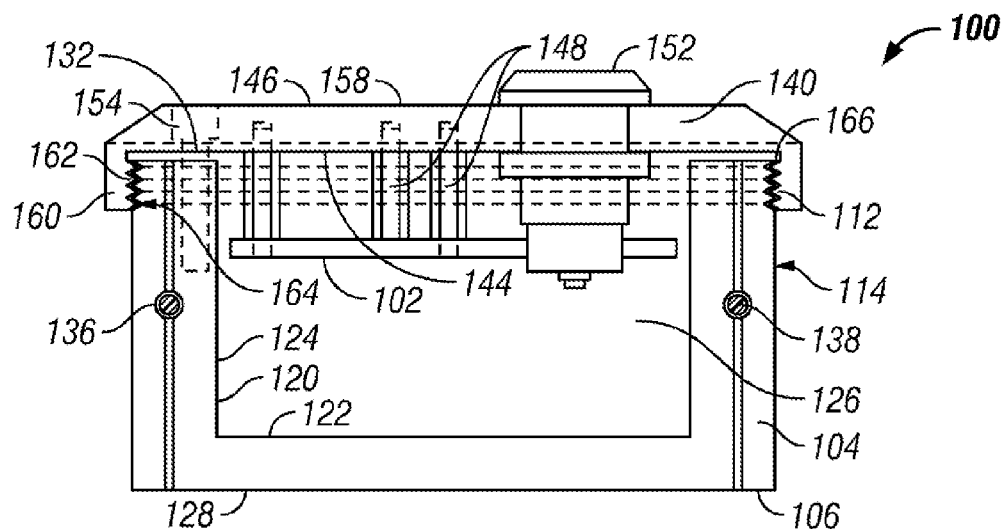
FIG. 6 is a cross sectional side view of an embodiment of a retainer.
Figure 7:
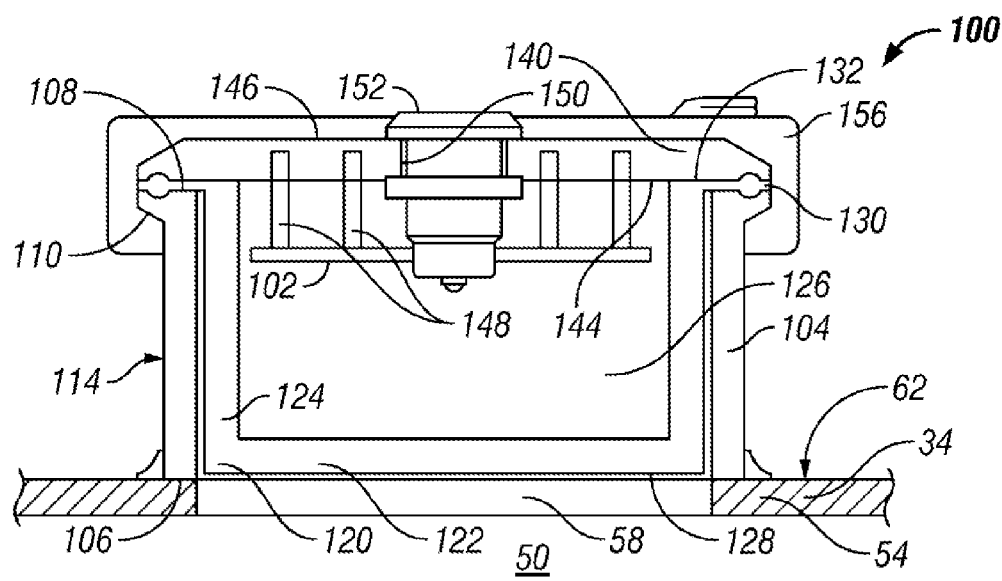
FIG. 7 is a cross sectional side view of an embodiment of a retainer affixed to a material separator.

Preferably, the first frame wall 54 includes a ferrule 104 with which the retainer 100 interfaces. The ferrule 104 has a first end 106 affixed to the outer surface 62 of the first frame wall 54 around the RF path 58 therethrough in such a way that the interface between the ferrule 104 and the first frame wall 54 is sealed, such as by welding. The ferrule 104 is preferably made from an electrically conductive material so that RF signals cannot pass therethrough. A flange 110 may extend outward from the second end 108 of the ferrule 104. Alternatively, the ferrule 104 may include one or more threads 112 helically surrounding the outer surface 114 proximate the second end 108, as shown in FIG. 6. While shown as having a circular cross sectional shape, it will be appreciated by a person of ordinary skill in the art that the ferrule may be of any cross sectional shape.

The housing 120 includes a tubular housing wall 124 having a cross sectional shape configured to complement the ferrule cross sectional shape. The housing wall 124 and the ferrule 104 are sealingly retained together. A housing faceplate 122 extends across a cross sectional area of the housing wall 124 and is affixed thereto to form a cup-like opening 126 segregated from the first chamber 50. The housing faceplate 122 is made from an RF transmissible material. When the housing wall 124 is retained within the ferrule 104, the housing 120 may be made from an RF-transmissible material or an RF shielding material. When the housing wall 124 is retained to the ferrule 104 at a first housing end 128 only, the housing wall 124 must be made from an RF-shielding material to prevent RF signals from being transmitted outside of the first chamber 50.

Figure 5:
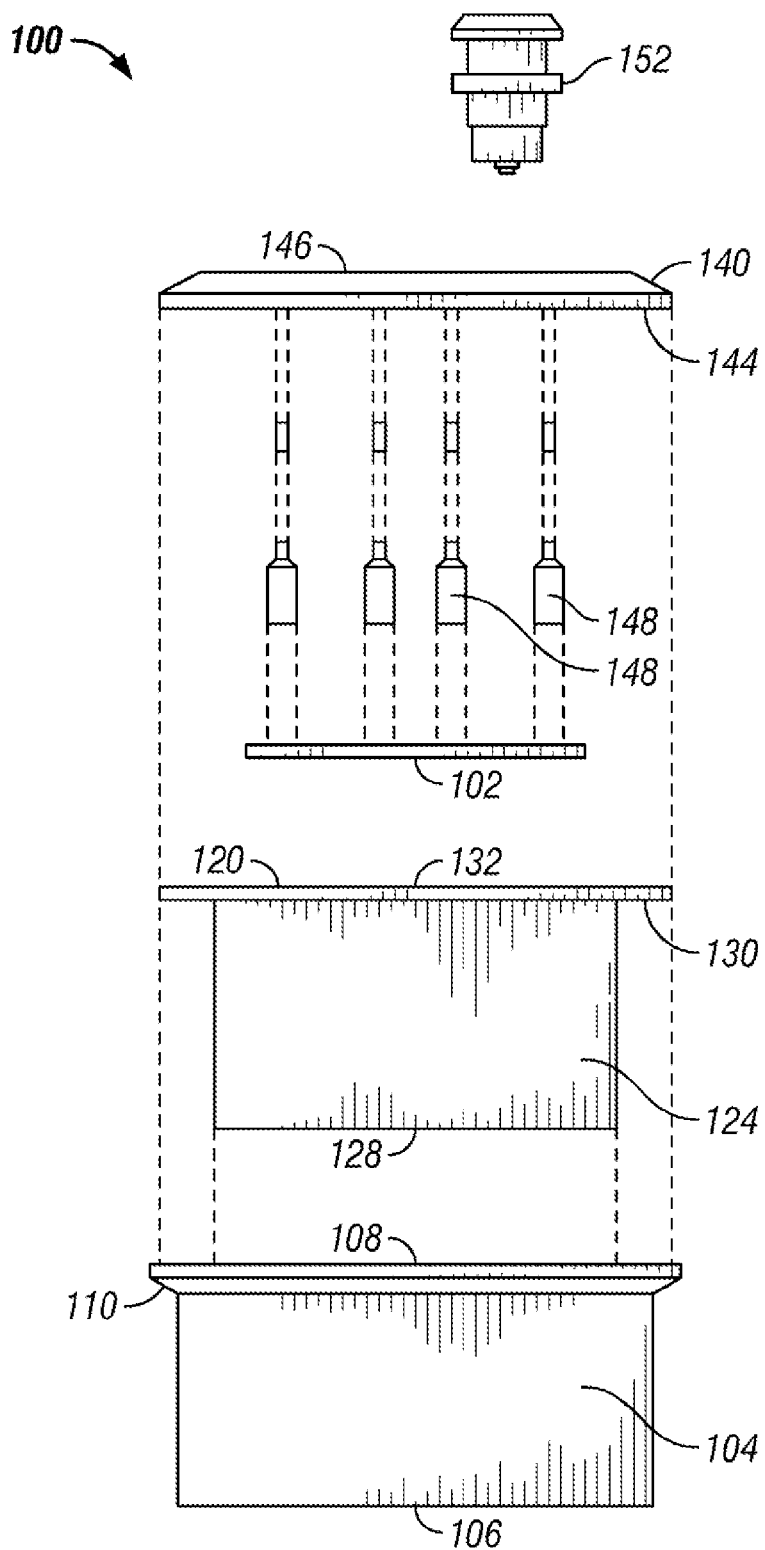
FIG. 5 is an exploded view of an embodiment of a retainer.
Figure 9:
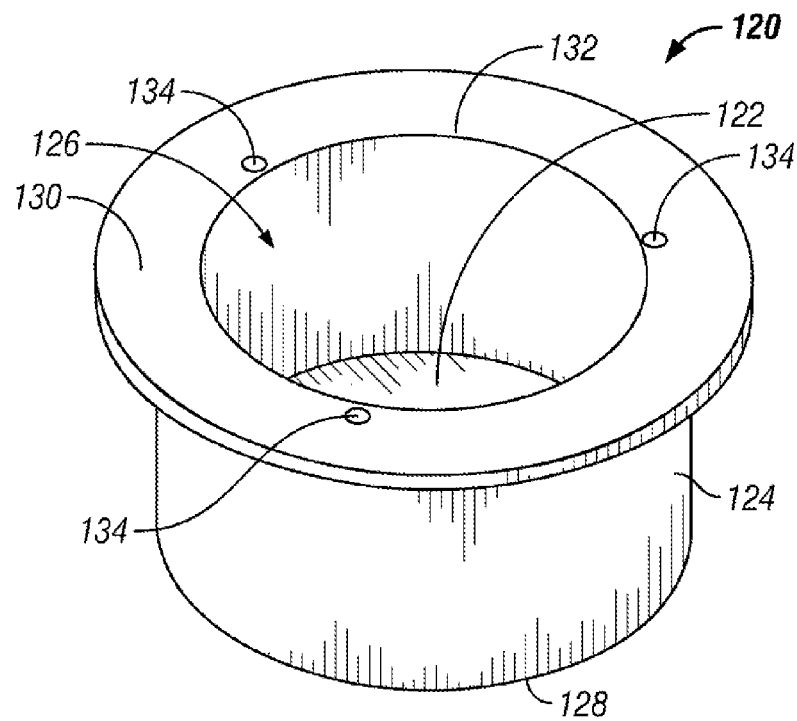
FIG. 9 is a perspective view of an embodiment of a housing.

In a first embodiment of the housing 120, depicted in FIG. 9, a housing flange 130 may extend from a second housing end 132. As shown in FIGS. 4 and 5, when the housing 120 is assembled to the ferrule 104, the housing flange 130 is positioned against the flange 110 of the ferrule 104. The housing 120 may include a plurality of holes 134 into the second housing end 132 into which threaded fasteners 142 may be placed to aid in the retention of the housing 120 to the cap 140 as will be described in more detail below.

Figure 10:
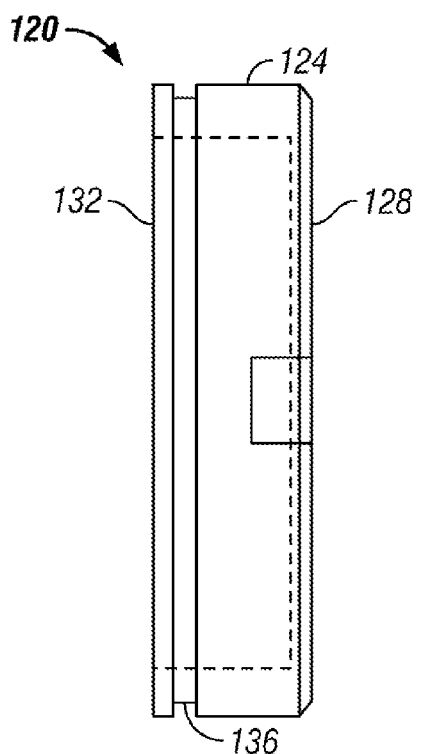
FIG. 10 is a side view of an embodiment of a housing.
Figure 11:
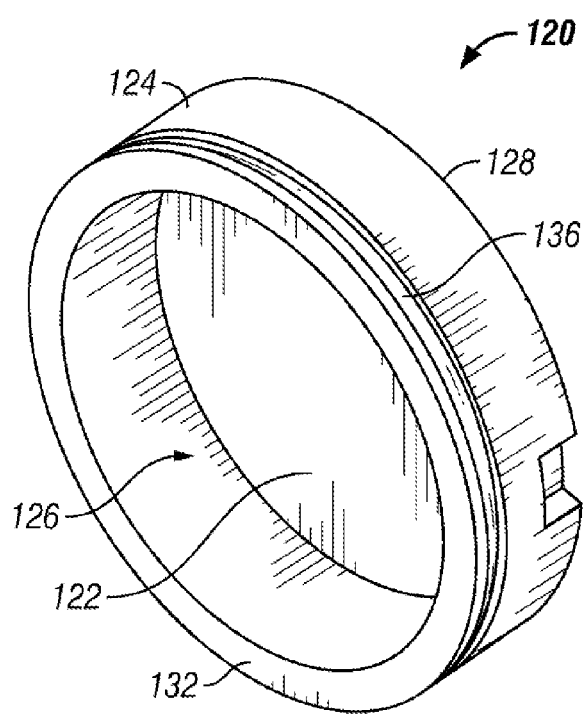
FIG. 11 is a perspective view of an embodiment of a housing.

In an alternative embodiment of the housing 120, depicted in FIGS. 10 and 11, the housing 120 does not have a flange. The housing wall 124 has a circumferential groove 136 within which a seal 138 may be seated to seal the interface between the interface between the housing wall 124 and the ferrule 104. The seal 138 retains the housing 120 in the desired location relative to the ferrule 104.

Figure 8:
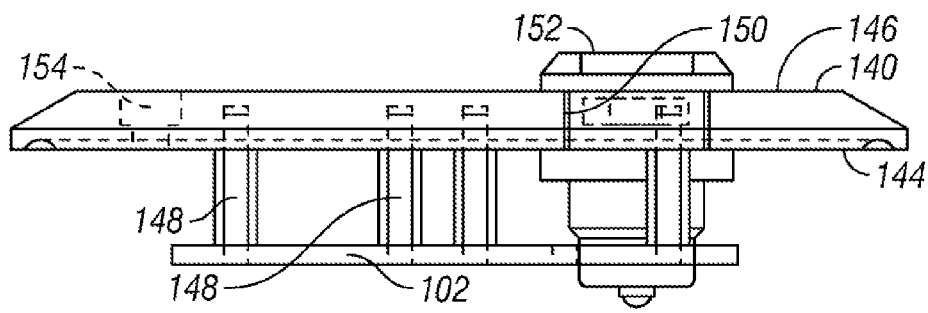
FIG. 8 is a side view of an embodiment of a cap and electronic communication device component.
Figure 14:
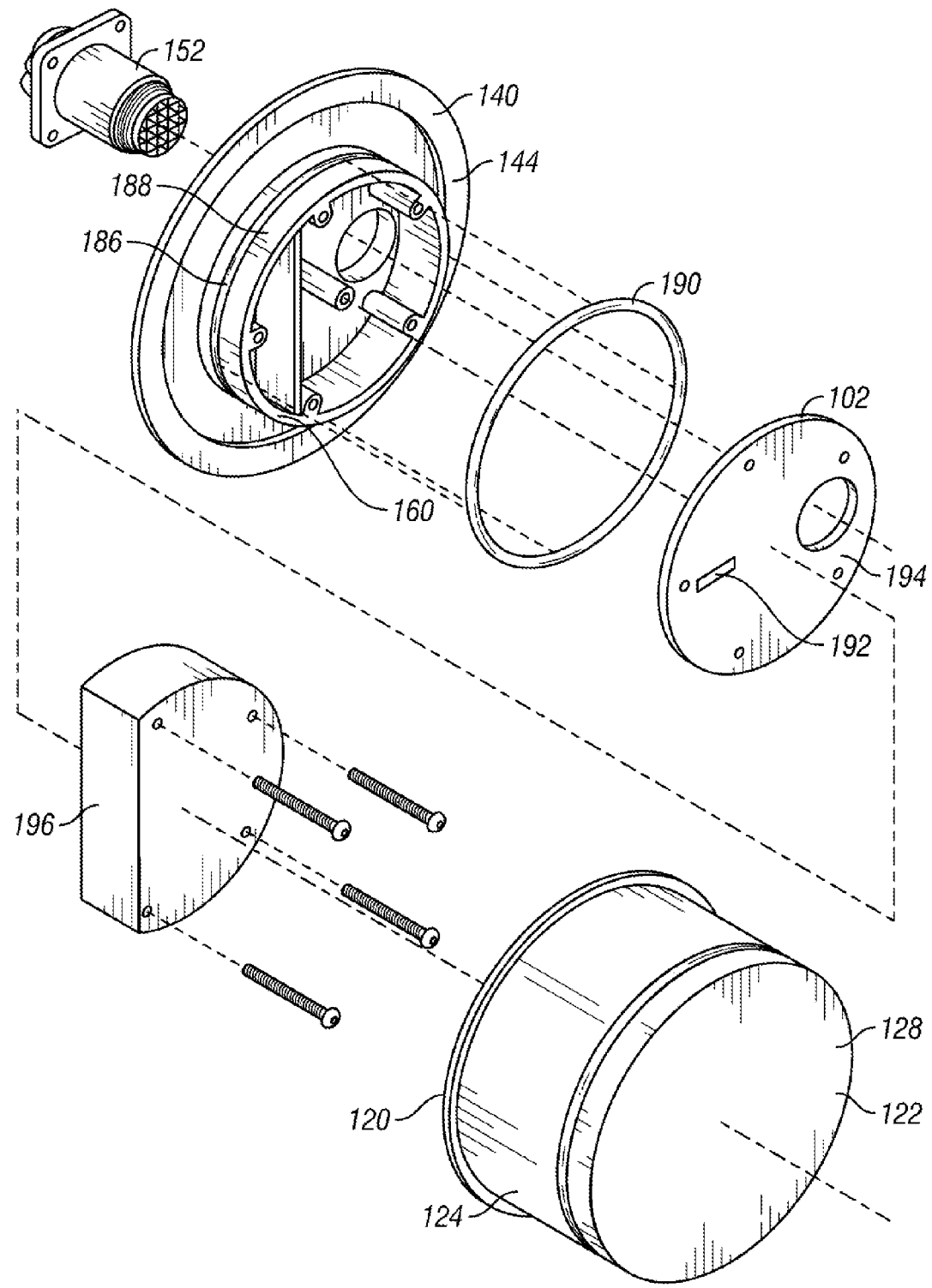
FIG. 14 is an exploded view of an embodiment of the retainer system.

The cap 140 covers the opening 126 in the housing 120 and should be made from an RF shielding material to prevent RF signals from passing into or out of the retainer through the cap 140. Referring to FIG. 8, a cap first side 144 faces into the opening 126, while a cap second side 146 faces outward. The cap 140 retains the electronic component 102 inside the opening 126 of the housing 120 at a predetermined distance 180 from the cap first side 144. This may be accomplished by having a plurality of standoffs 148 retained by or integrally formed with the cap 140, extending from the cap first side 144. The standoffs 148 are used to retain the electronic component 102 inside the opening 126 in the housing 120, as shown in FIGS. 4, 6-9. Alternatively the cap 140 may include a cap skirt 160 and/or screw bosses 184 to maintain the predetermined distance 180 between the cap first side 144 and the electronic component 102, as shown in FIG. 14.

A connector orifice 150 through the cap 140 retains a connector 152. The connector 152 interfaces with the electronic component 102 and is operable to communicate electronic signals between the component 102 and an external electronic device 170 (shown in FIG. 13).

The cap 140 is retained against the ferrule 104 to shield RF signals from entering or escaping the retainer. Examples of ways to retain the cap 140 to the remainder of the retainer assembly such that RF signals are shielded from being emitted outside the retainer are described below.

Cap 140 may have a plurality of fastener orifices 154 through it. The fastener orifices 154 correspond in location to the holes 134 in the housing 120. Threaded fasteners 142 may be used to secure the cap 140 to the housing second end 132 to ensure that the electronic component 102 is sealed inside the opening 126 in housing 120.

Referring again to FIGS. 3 and 4, a clamp band 156 may be used to hold the cap 140 and flange 110 of the ferrule 104 together. When the embodiment of the housing 120 including a housing flange 130 is used, the housing flange 130 may be held between the cap first side 144 and the flange 110 of the ferrule 104. When the embodiment of the housing 120 without a housing flange is used, the cap 140 and the flange 110 of the ferrule 104 are held together. A seal (not shown) may be included in the latter embodiment between the flange 110 and cap 140.

In an alternative embodiment of the retainer 100, depicted in FIG. 6, the ferrule 104 includes one or more threads 112 helically surrounding the outer surface 114 proximate the second end 108. The cap 140 includes a cap end wall 158 and cap skirt 160. The cap skirt 160 extends from the cap end wall 158 and includes one or more helical grooves 162 around an inner surface 164. The helical grooves 162 are sized and located to receive the threads 112 on the second end 108 of the ferrule 104, thus permitting the cap 140 to be twisted onto the ferrule 104. A sealant material 166 may be used between the cap 140 and the ferrule 104 to prevent contaminants from entering the opening 126 in the housing 120.

Another alternative is depicted in FIG. 14. The cap skirt 160 is located radially inward from the cap perimeter and has an external groove 186 around its outer surface 188. A gasket 190, such as an o-ring fits within the groove 186. When the cap 140 is pressed toward the housing 120, the cap skirt 160 fits within the housing wall 124. The gasket 190 provides a sealed interference fit between the cap skirt 160 and the housing wall 124 such that the cap first side 144 is retained against the second end 108 of the ferrule 104.

In another alternative, not depicted, the cap skirt 160 has one or more helical threads around the wall outer surface. The housing wall 124 includes one or more corresponding helical grooves along its inner surface that are sized and located to receive the threads on the cap wall. The cap 140 may be twisted to engage the corresponding threads in a conventional manner.

The receiver 46 component will include a trace, or antenna, 192. It has been found to be advantageous to shield the antenna 192 from the remainder of the circuit board 194 to prevent noise from unnecessarily triggering a signal received by the antenna that is falsely interpreted as a screen break detection. A shield 196 may be constructed of a conductive material and affixed over the portion of the circuit board 194 including the connector 152 and other electronics, thereby shielding certain circuit board components from the antenna 192.

Figure 15:
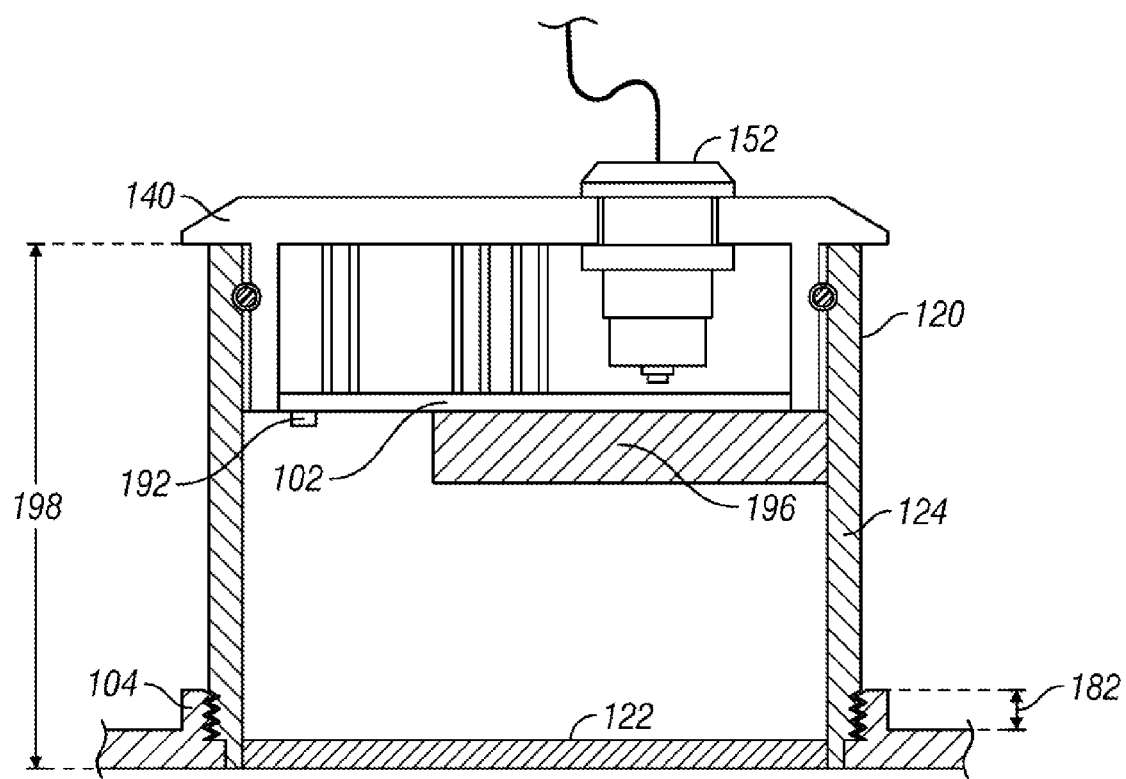
FIG. 15 is a cross sectional view of an embodiment of the retainer system.

In an alternative embodiment, shown in FIG. 15, the ferrule 104 may extend outward from the first chamber wall 54 a distance 182 less than the length 198 of the housing 120. The ferrule 104 may provide an interface surface to which the housing 120 may be attached. In such an embodiment, the housing wall 124, or walls may be an RF non-transmissible material to prevent RF signals from being emitted outside of the first chamber 50. Alternatively, the cap skirt 160 may be formed from an RF non-transmissible material and extend over the component 102 to the housing faceplate 122. As with all of the retainer 100 embodiments, the housing faceplate 122 must be made from an RF-transmissible material to provide RF signals to the first chamber 50.

The retaining system 200 for the transmitter 44 and the receiver 46 used to detect an RF path through a porous element is shown in FIGS. 12 and 13. A first retainer 202 is affixed around the RF path 58 through the first frame wall 54 and a second retainer 204 is affixed around the RF path 60 through the second frame wall 56. It will be appreciated by one of skill in the art that the transmitter 44 may be retained by the first retainer 202 and the receiver 46 may be retained by the second retainer 204 or vice versa.

The first and second retainers 202 and 204 each have a structure as described. The first retainer 202 may fit within a first ferrule 104a having a first end 106a and a second end 108a. The first end 106a is affixed to the outer surface 62 of and around the RF path 58 through the first frame wall 54. The first ferrule 104a may include a flange 110a at the second end 108a.

The first retainer 202 includes a first housing 120a sealingly retained within the first ferrule 104a. The first housing 120a is sealed against a first cap 140a such that the transmitter 44 is sealed within the first housing 120a and the first cap 140a. The first housing 120a includes a faceplate 122a through which RF signals are transmissible. The faceplate 122a provides a physical barrier between the transmitter 44 and the first chamber 50. The first cap 140a is held against the ferrule flange 110a, if included. Alternatively, the first housing 120a may include a housing flange 130a at the housing second end 132a, which may be retained between the flange 110a of the first ferrule 104a and the first cap 140a, should the first ferrule 104a include a flange 110a. A first clamp band 156a may be used to hold the first cap 140a to the flange 110a.

The second retainer 204 may fit within a second ferrule 104b having a first end 106b and a second end 108b. The first end 106b is affixed to the outer surface 64 of and around the RF path 60 through the second frame wall 56. The second ferrule 104b may include a flange 110b at the second end 108b.

The second retainer 204 includes a second housing 120b sealingly retained within the second ferrule 104b. The second housing 120b is sealed against a second cap 140b such that the receiver 46 is sealed within the second housing 120b and the second cap 140b. The second housing 120b includes a faceplate 122b through which RF signals are transmissible. The faceplate 122b provides a physical barrier between the receiver 46 and the second chamber 52. The second cap 140b is held against the ferrule flange 110b, if included. Alternatively, the second housing 120b may include a housing flange 130b at the housing second end 132b, which may be retained between the flange 110b of the second ferrule 104b and the second cap 140b. A second clamp band 156b may be used to hold the second cap 140b to the flange 110b.

Alternatively, as is depicted in FIG. 6, the first ferrule 104a and/or the second ferrule 104b may include one or more threads 112 around the outer surface 114 near the second end 108a, 108b. The first cap 140a may include a first cap end wall 158a from which a first cap skirt 160a extends. One or more helical grooves 162 may be located on the inner surface 164a of the first cap skirt 160a, corresponding to the location and size of the threads 112. Likewise, the second cap 140b may include a second cap end wall 158b from which a second cap skirt 160b extends. One or more helical grooves 162 may be located on the inner surface 164b of the second cap skirt 160b, corresponding in location and size to the threads 112. A sealant material 166 may be used between the threads 112 and grooves 162 to seal the interface.

As the first cap 140a and first ferrule 104a are preferably made of an RF shielding material, the RF signals from the transmitter 44 are directed through the first housing faceplate 122a and into the first chamber 50. The command to send the signal may be sent from an external device 170 through the first connector 152a retained by the first cap 140a. On the opposing side of the screen 22, the receiver 46 seeks to detect the RF signal from the transmitter 44. Because the first and second chambers 50 and 52 are each bounded by RF shielding components, the RF signal will only pass between the first and second chambers 50 and 52 when a tear has developed in the screen 22 large enough for the RF signal to pass. When the receiver 46 receives an RF signal through the second housing faceplate 122b, an electronic communication is sent to the external device 170 through the second connector 152b, which is retained by the second cap 140b.

While described in terms of two chambers 50, 52 separated by a single screen 22, one of skill in the art will appreciate that two receivers may be used to detect microwaves from a single transmitter 44 when two screens are present in the separator 10. Thus, a single transmitter may be used with a detector in each adjacent chamber to detect screen breaks between them. Further, when additional screens are in place in the separator, an additional transmitter or transmitters and additional receivers may be used as necessary to ensure that each screen is being monitored by the screen break detector.

While the claimed subject matter has been described with respect to a limited number of embodiments, those skilled in the art, having benefit of this disclosure, will appreciate that other embodiments can be devised which do not depart from the scope of the claimed subject matter as disclosed herein.

Accordingly, the scope of the claimed subject matter should be limited only by the attached claims.

What is claimed is:

1. A retaining system for a transmitter and a receiver for detecting an RF path through a porous element in a material separator, wherein the material separator includes a first frame having a first frame wall and a second frame having a second frame wall, wherein the porous element is received between the first frame wall and the second frame wall such that a first chamber and a second chamber are defined, the retaining system comprising:
   a first retainer within which the transmitter is housed, wherein the first retainer is affixed about an RF path through the first frame wall and provides a barrier to RF signals outside of the RF path through the first frame wall;
   wherein the first retainer comprises:
      a first ferrule having a first end affixed around the RF path through the first frame wall and a second end extending outward from the first frame wall;
      a first housing sealingly retained within the first ferrule and separating the transmitter from the first chamber;
      a first cap sealingly retained against the second end of the first ferrule and retaining the transmitter within the first housing and having a connector opening therethrough retaining a transmitter communication connector providing data exchange between the transmitter and an external device; and
   a second retainer within which the receiver is housed, wherein the second retainer is affixed about an RF path through the second frame wall and provides a barrier to RF signals outside of the RF path through the second frame wall.

2. A retainer system as in claim 1, wherein the second retainer comprises:
   a second ferrule having a first end affixed around the RF path through the second frame wall and a second end extending outward from the second frame wall;
   a second housing sealingly retained within the second ferrule and separating the receiver from the first chamber;
   a second cap sealingly retained against the second end of the second ferrule and retaining the receiver within the second housing and having a connector opening therethrough retaining a receiver communication connector providing data exchange between the receiver and an external device.

3. A retainer system as in claim 1, wherein the first ferrule and the second ferrule are each formed from an RF blocking material; and
   wherein the first housing has a faceplate between the transmitter and the first chamber and the second housing has a faceplate between the receiver and the second chamber, each faceplate being formed from an RF transmissible material.

4. A retainer system as in claim 1, wherein the first ferrule includes an outwardly extending flange to which the first cap is sealingly retained; and
   wherein the second ferrule includes an outwardly extending flange to which the second cap is sealingly retained.

5. A retainer system as in claim 4, wherein the first and second housings each include an outwardly extending housing flange, the housing flange of the first housing sealingly retained between the flange of the first ferrule and the first cap and the housing flange of the second housing sealingly retained between the flange of the second ferrule and the second cap.

* * * * *